United States Patent [19]
Kruger et al.

[11] Patent Number: 5,382,406
[45] Date of Patent: Jan. 17, 1995

[54] STERILE FILLING METHOD

[75] Inventors: Robert J. Kruger, McHenry; Joaquin Mayoral, Downers Grove, both of Ill.

[73] Assignee: Abbott Laboratories, Abbott Park, Ill.

[21] Appl. No.: 93,297

[22] Filed: Jul. 16, 1993

Related U.S. Application Data

[63] Continuation-in-part of Ser. No. 510,317, Apr. 17, 1990, abandoned.

[51] Int. Cl.⁶ ............................................. B65B 55/10
[52] U.S. Cl. ..................................... 422/28; 422/103; 53/425; 53/426; 53/471
[58] Field of Search ................. 422/21, 22, 26, 27, 422/28, 102, 103, 33–37; 53/425, 426, 468, 469, 471, 473

[56] References Cited

U.S. PATENT DOCUMENTS

| | | | |
|---|---|---|---|
| 3,340,671 | 9/1967 | Loo | 53/426 |
| 3,514,919 | 6/1970 | Ashton et al. | 53/426 |
| 3,531,908 | 10/1970 | Rausing et al. | 53/426 |
| 4,494,363 | 1/1985 | Rica et al. | 53/426 |
| 4,805,378 | 2/1989 | Anderson | 53/426 |

FOREIGN PATENT DOCUMENTS

| | | |
|---|---|---|
| 0452780 | 10/1991 | European Pat. Off. . |
| 8602906 | 5/1986 | WIPO . |

OTHER PUBLICATIONS

Block, S. S. "Disinfection, Sterilization and Preservation", 3d ed. Lea & Febiger, 1983. pp. 3–4, 47 and 89–92.

*Primary Examiner*—Jeffrey R. Snay

[57] ABSTRACT

The present invention is directed to a method for the on-line sterile filling of a container with a sterile solution from a filling nozzle in a filling head. A container having an open end and a hollow body portion for receiving the sterile solution is provided. The container also includes an access passageway tube having first and second ends and a pierceable septum sealing the passageway at an intermediate position within the tube. The first open end of the access passageway tube is sealed in the open end of the container so as to close the hollow body portion of the container, which is then sterilized. Later, before on line filling, the second end of the access passageway tube is isolated from the surrounding environment by axially advancing and sealably seating the filling head at the second end of the access passageway tube. The isolated end of the access passageway tube is then sterilized for a time period sufficient to reduce the viable micro-organism population present to a predetermined level. Then a filling nozzle is advanced from the filling head through the isolated and sterilized end of the passageway tube and pierces the septum of the tube. After the sterilized hollow body portion is filled with the sterile solution, the access passageway is sealed between the hollow body portion and the filling nozzle.

4 Claims, 6 Drawing Sheets

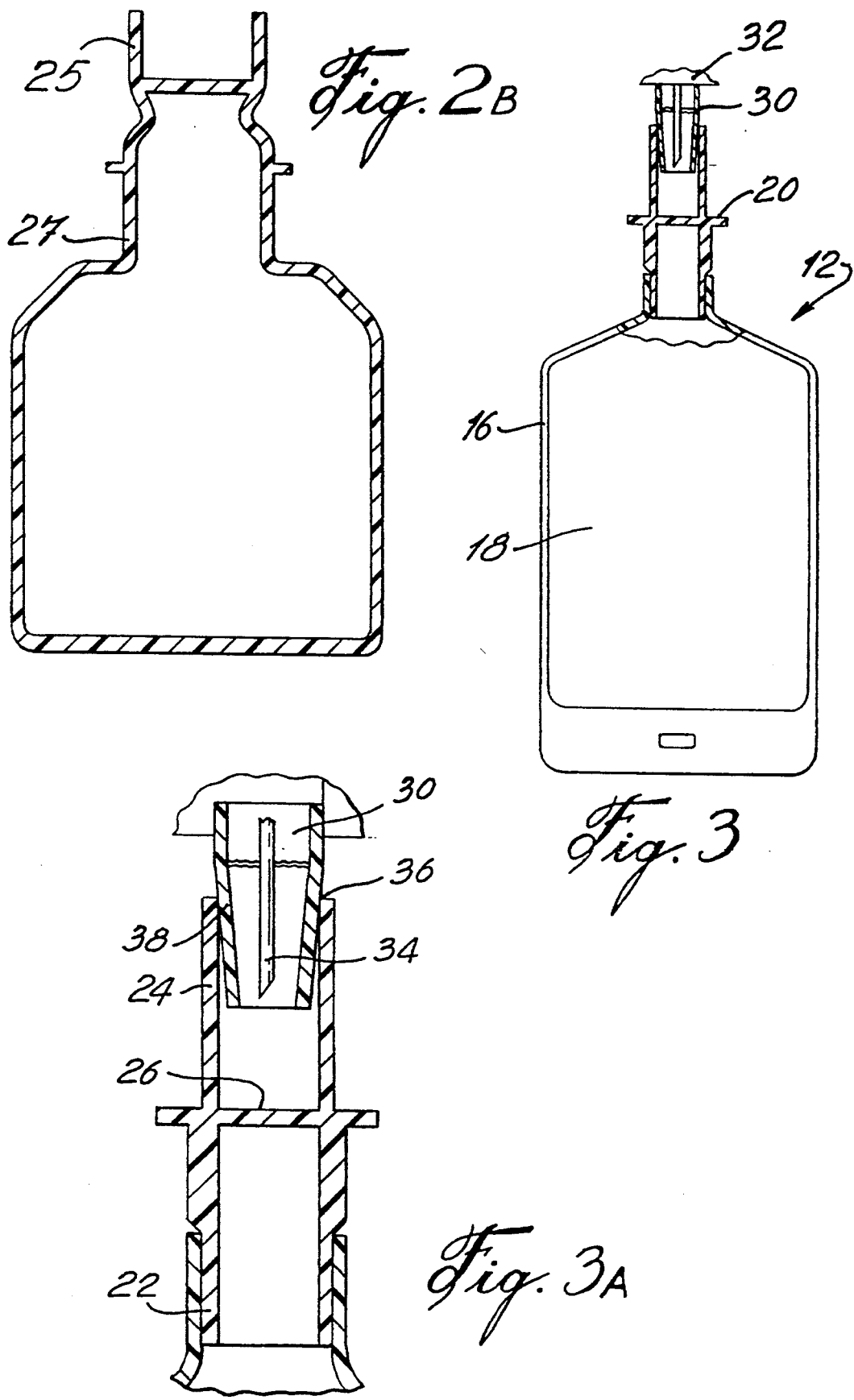

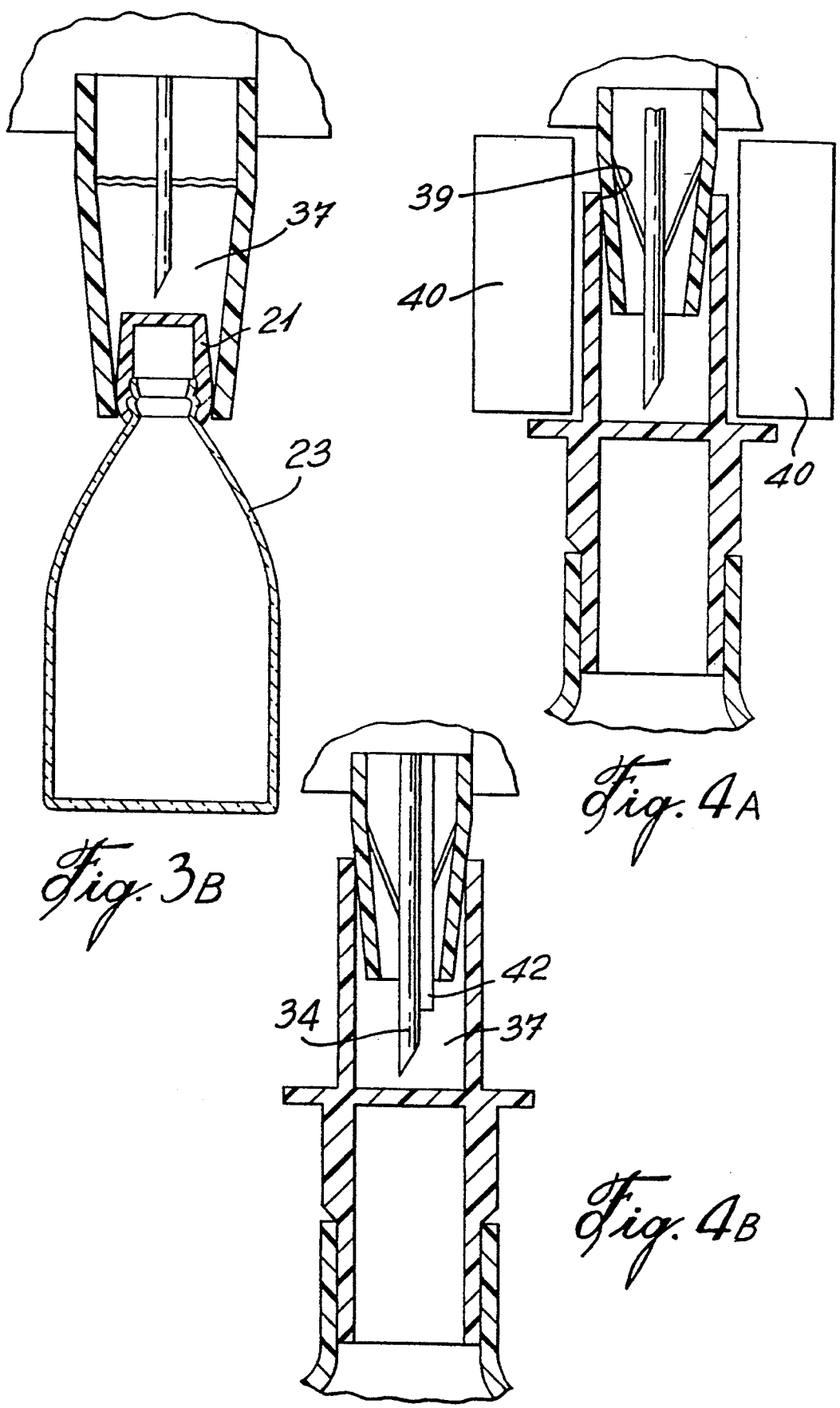

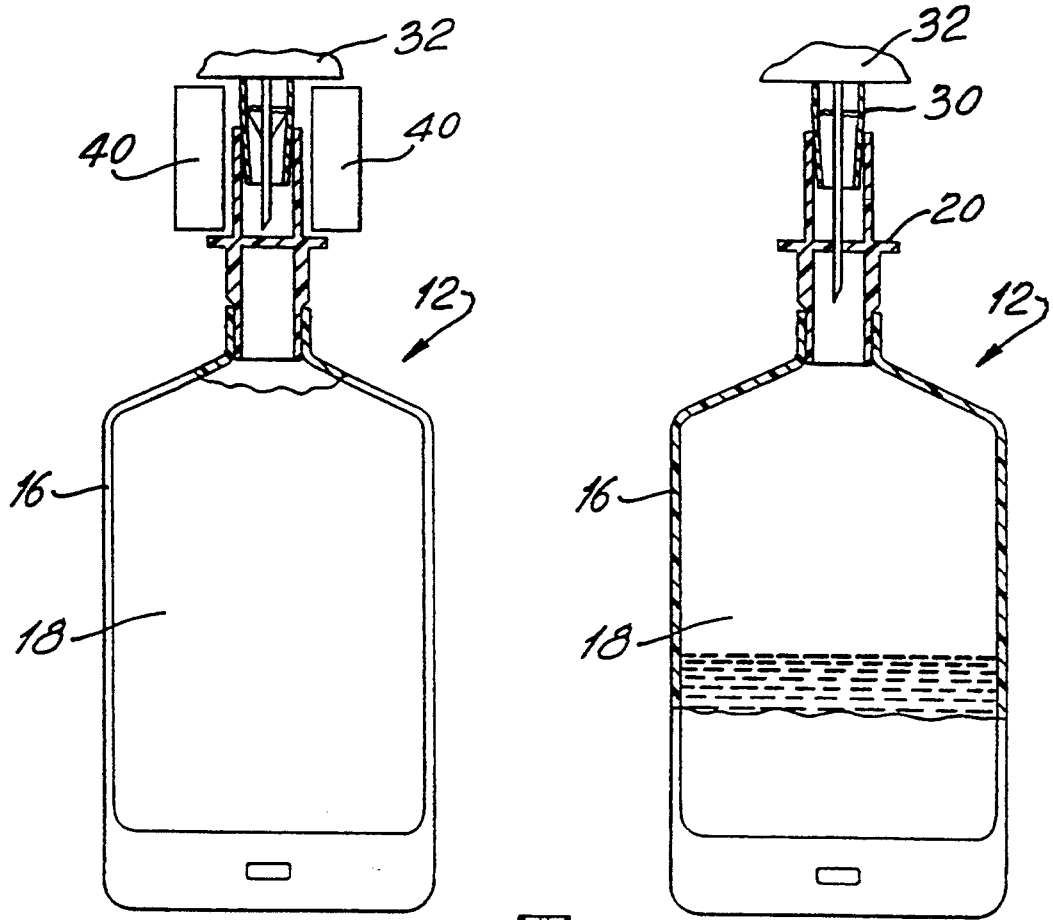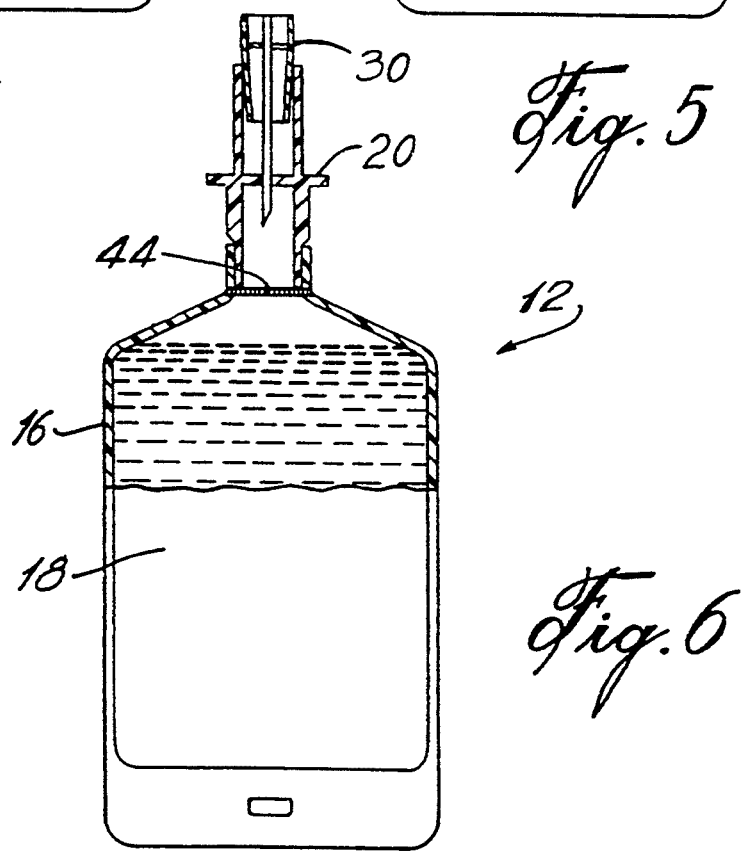

5,382,406

STERILE FILLING METHOD

This application is a continuation-in-part of commonly assigned pending U.S. patent application Ser. No. 07/510,317, filed Apr. 17, 1990, and now abandoned, entitled "Method for Sterilizing an Enclosure with Noncondensing Hydrogen Peroxide-Containing Gas." The benefit of the filing date of this prior application is hereby claimed under 35 USC §120.

FIELD OF THE INVENTION

The present invention relates generally to a method and apparatus for the sterile filling of medical solutions, and more particularly to a method and apparatus that utilizes the on-line sterilization capability of an access passageway to facilitate the subsequent on-line sterile filling with a sterile medical solution of a pre-sterilized empty container.

BACKGROUND OF THE INVENTION

Parenteral solutions, such as the medical solutions administered in intravenous therapy for example, must be sterile when administered to the patient, and therefore must be sterile when packaged and stored. These sterile solutions were originally packaged in glass bottles and more recently in flexible containers such as plastic film bags. Flexible containers are preferred over glass containers due to advantages such as weight, ease of handling, disposability, and other considerations.

Conventionally the flexible container is fabricated and the solution is sealed in the container. Then the container and solution is terminally sterilized. The flexible container may be further packaged, shipped and then stored until needed.

The flexible container is manufactured of a plastic film or other material that is suitably compatible with the medical solution so as to minimize reaction with the solution or allow degradation and/or loss of potency during manufacture and/or storage. Suitable plastic material includes heat sealable PVC film for example.

A terminal sterilization method is selected so that the process is compatible with both the material of the flexible container and the medical solution therein. Suitable terminal sterilization methods include radiation sterilization and steam autoclaving, for example.

However, an increasing number of parenteral administered solutions, such as the new, biotechnically produced drugs, are not necessarily compatible with any combination of the presently known flexible containers and terminal sterilization processes currently in use. For example, some therapeutic solutions packaged in flexible containers lose their potency or change their composition if they are subjected to terminal sterilization by the traditional energy or chemical sterilization procedures. Energy sterilization processes include application of heat such as by steam autoclaving, or irradiation with Gamma, X-ray, microwave, plasma, for example. Chemical sterilization may include sterilization by liquid or vapor hydrogen peroxide, ethylene oxide (ETO), phenol, ethanol, or sodium hypochlorite for example.

The United States Food and Drug Administration (FDA) is currently recommending that all medical and surgical products be sterilized to a microbial survival probability of $10^{-6}$, an assurance that there is less than one chance in one million that viable micro-organism, such as viruses, bacteria, and spores, are present in the sterilized product.

For a general discussion of sterilization and techniques therefor. see *The United States Pharmacopeia XXII*, ch. 1211, pp 1705 et seq., Atkinson et al., *Biochemical Engineering and Biotechnology Handbook*, Stockton Press, New York, N.Y. (1983), pp. 875–886, and Demain et al., *Manual of Industrial Microbiology and Biotechnology*, American Society for Microbiology, Washington, D.C. (1986), pp. 345–362.

Thus there is a need for an alternative sterilization process that can be economically, efficiently, and safely used on-line with current filling processes.

There is also a need for a sterilizing and filling process that avoids using expensive packaging materials, and costly manufacturing and/or sterilization processes for large or small volume sterile packaging of known and new drugs for parenteral administration that have unique and sensitive characteristics, such as for example some of the biotechnically produced solutions or drugs.

SUMMARY OF THE INVENTION

The present invention provides efficient on-line sterilization of an access passageway to a container, including flexible, semi-rigid, or rigid containers and allows for the subsequent sterile filling of the container during an on-line process. The access passageway sterilization process may be accomplished by any one of the variety of known sterilization processes including gas sterilization, vapor sterilization, thermal sterilization, radiation sterilization, plasma sterilization, and/or chemical agent sterilization.

The present method has the advantage of achieving a high degree of sterilization efficiency in a relatively short time, since it takes only seconds to sterilize the small volume of the access passageway of a pre-sterilized container. The on-line sterilization of the access passageway can be performed at fluid filling line speeds, thus facilitating use in a sterile filling process.

The present invention is directed to a method and apparatus for the on-line sterile filling of a container, including flexible, semi-rigid, or rigid containers, with a sterile solution from an on-line filling mechanism. The container has an open end and a hollow body portion for receiving the sterile solution. The container also includes an access passageway tube having first and second ends and a pierceable septum sealing the passageway at an intermediate position within the tube. The first open end of the access passageway tube is sealed to the open end of the container so as to close the hollow body portion of the container. After the hollow body portion is closed, the container is sterilized, either as a separate operation before the filling operation (i.e. pre-sterilized off-line) or as a step in the filling operation (i.e. on-line). In either situation, when the empty sterilized containers arrive on-line at the filling station, the second end of the access passageway tube is isolated from the surrounding environment by axially advancing and sealably seating the filling head to the second end of the access passageway tube. The isolated end of the access passageway tube is then sterilized on-line for a time period sufficient to reduce the viable micro-organism population present to a predetermined acceptable level. Due to the small volume of the access passageway, this sterilization can be achieved at on-line filling speeds. Then a filling nozzle is advanced from the filling head through the isolated and sterilized end of the access passageway tube. The nozzle pierces the septum of the tube and the sterilized hollow body portion of the container is filled with the sterile solution. Before the nozzle is withdrawn from the septum, the filled container is sealed at a point on the container between the hollow body portion and the inserted filling nozzle. The unneeded portion of the access passageway is then detached and the sterile container containing sterile solution is ready for further processing or use.

This invention, both as to its method of operation and apparatus, will be best understood from the following description of specific embodiments when read in connection with the accompanying drawings.

BRIEF DESCRIPTION OF THE DRAWINGS

FIG. 2B is a schematic representation of an integral access passageway fabricated with a semi-rigid container;

FIG. 3 is a schematic representation of a filling head mechanism sealingly positioned at the exposed end of the access passageway tube;

FIG. 3A is an enlarged view of the access passageway tube of FIG. 3;

FIG. 3B is an enlarged view of the alternative access passageway tube of FIG. 2A sealingly contacted by an alternative filling head;

FIG. 4 is a schematic representation of the access passageway tube during sterilization by a representative on-line energy sterilization process;

FIG. 4A is an enlarged view of the access passageway tube of FIG. 4;

FIG. 4B is an enlarged view of the access passageway tube of FIG. 4 during sterilization by an alternative on-line chemical sterilization process;

FIG. 5 is a schematic representation of a filling nozzle piercing the septum of the access passageway tube;

FIG. 6 is a schematic representation of a seal produced at the neck portion of the filled flexible container prior to the filling nozzle being withdrawn from the septum;

DETAILED DESCRIPTIONS OF THE PREFERRED EMBODIMENTS

The sterile filling system for practicing the method of this invention is schematically illustrated in FIGS. 1-8.

Figure 1:
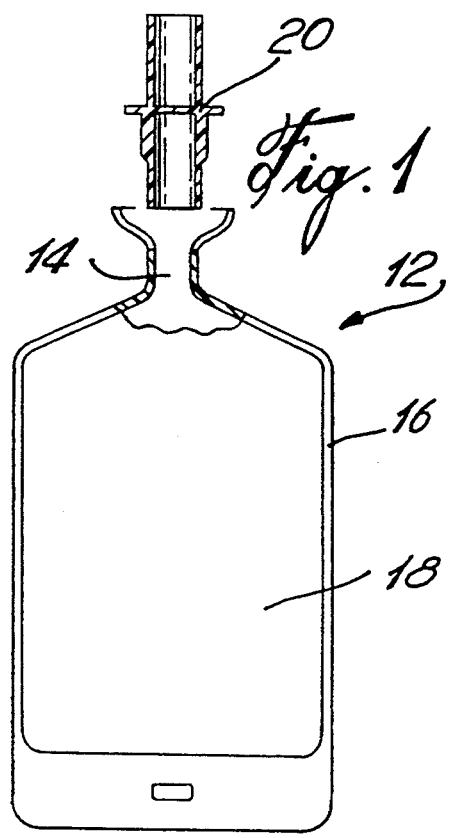
FIG. 1 is a schematic representation of a flexible container having an open end aligned but not attached to a separately fabricated access passageway tube.

A container, such as a flexible plastic film bag 12 in FIG. 1, or a fabricated paperboard composite container, or a semi-rigid blow molded container, or a rigid glass bottle, is manufactured with an open end 14. For discussion purposes, the container 12 will be described as a flexible container fabricated from two sheets of PVC plastic film, for example. However, other flexible, semi-rigid and rigid container embodiments are also considered to be within the scope of this invention. The two sheets of plastic film are sealed together along the edges by any know sealing technique, such as radio frequency (RF), ultrasonic or thermal welding. The perimeter seal 16 extends along substantially the circumferential perimeter of the flexible container, except for the opening 14, and defines a hollow body portion 18. A hollow body portion is common to all container embodiments of this invention, whether flexible, semi-rigid, rigid or otherwise fabricated.

A separately manufactured access passageway tube 20 is fabricated by molding or extruding a plastic material such as polyethylene or PVC, for example. The access passageway tube 20 is adapted to fit and align with the container opening 14. Alternatively, the access passageway may be fabricated integrally with the container such as by known blow molding or injection molding processes.

Figure 1A:
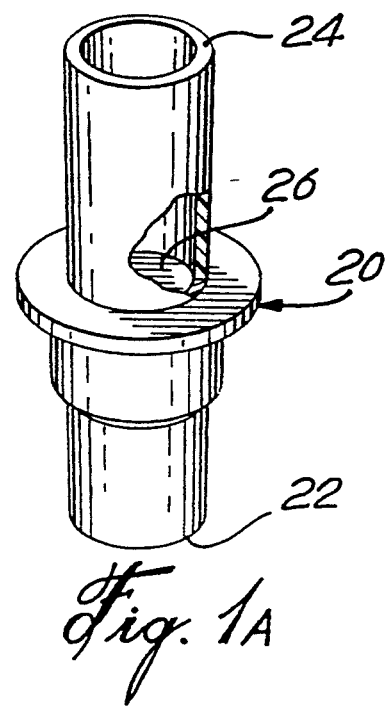
FIG. 1A is an enlarged perspective view of the separately fabricated access passageway tube of FIG. 1.

Referring now to FIG. 1A, the access passageway tube 20 is essentially a hollow tube, preferably cylindrical, although other shapes such as an oval, square, diamond, or triangle are equally useable. In the preferred embodiment, the access passageway tube 20 has two opposed open ends, including a first end 22 and a second end 24. The tube also includes a pierceable septum 26 at an intermediate position within the hollow passageway which completely divides and closes the passageway.

Figure 2:
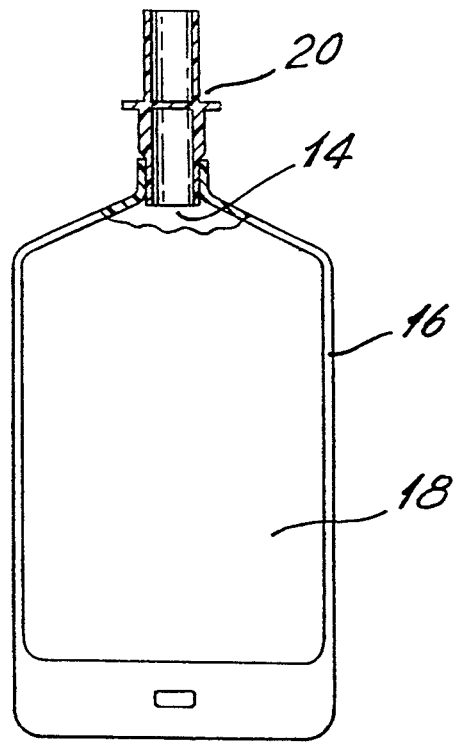
FIG. 2 is a schematic representation of the separately fabricated access passageway tube sealingly attached and closing the open end of the flexible container.
Figure 2A:
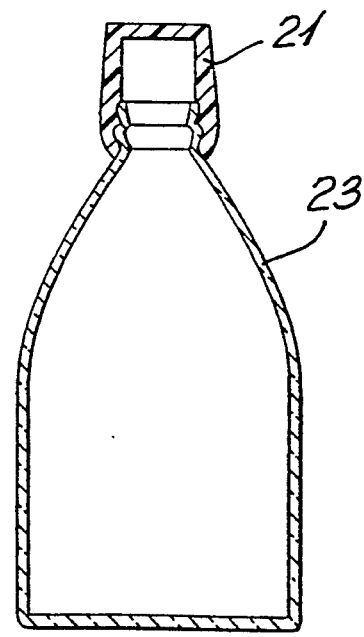
FIG. 2A is a schematic representation of an alternative separately fabricated access passageway tube sealingly attached and closing the open end of a rigid glass container.

As shown in FIG. 2, the access passageway tube 20 is permanently attached and sealed to the open end 14 of the container. As shown in FIGS. 2A, a slightly modified access passageway tube 21 is attached and sealed to the outside open end of a glass bottle 23. As shown in FIG. 2B a further modified integral access passageway 25 is fabricated with a semi-rigid blow molded container 27. All of the sealed, empty containers may now be sterilized by any known suitable on-line or off-line sterilizing process prior to being filled with a sterile solution.

Referring now to FIG. 3 and 3A, a filling head 30 of the filling mechanism 32 is axially moved into sealing contact with the second end 24 of the access passageway attached to the container.

The second end 24 of the access passageway 20 is secured in an airtight manner, and the closed volume within the sealed chamber 37 can now be sterilized. A circumferential seal is formed at 36 when the distal, tapered end of the nozzle mandrel 38 with the filling nozzle 34 therein mates with or is removably received at the second end 24 of the access passageway 20. The sealed chamber 37 of the access passageway 20 is isolated from the environment to facilitate fast and efficient sterilization. An alternative embodiment is shown in FIG. 3B.

Referring to FIGS. 4 and 4A, the access passageway is sterilized on-line by passing through an energy sterilization unit such as shown schematically by blocks 40 on both sides of the processing line.

Alternatively, as seen in FIG. 4B, the access passageway can be chemically sterilized with a vapor or liquid introduced into the sealed chamber 37 by lumen 42 associated with the filling nozzle 34. Evacuation and purging can also be accomplished through lumen 40 or additional lumen as needed.

Figure 5A:
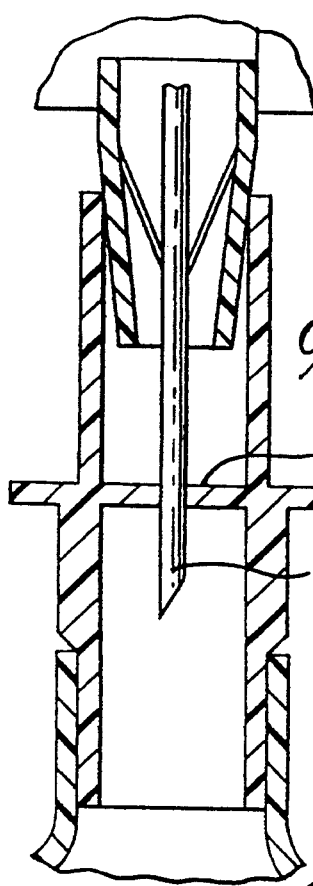
FIG. 5A is an enlarged view of the access passageway tube of FIG. 5.

After the access passageway 20 is sterilized, the pierceable septum 26 of passageway is penetrated by the filling nozzle 24, as shown in FIG. 5 and 5A. The filling nozzle 34 provides fluid flow communication with a sterile fluid source connected to the filling mechanism 32.

In FIG. 4, the sterilization passageway is defined by the mandrel 38 in cooperation with the open end 24 when the distal, tapered end of the mandrel is received therein. The tapered peripheral of mandrel 38 engages the distal end portion of end 24 to provide a circumferential airtight seal 39.

Initially filling nozzle 34 is positioned above septum 26 while the access passageway is sterilized. The access passageway 20 can be sterilized, along with that portion of nozzle 34 that is situated within the passageway, with subsequent evacuation and flush purge cycles as required for the contemplated filling operation for the container 12.

Since the container has been pre-sterilized, when the filling nozzle 34 pierces septum 26, the sterile container 12 can be filled with the desired sterile solution.

Figure 6A:
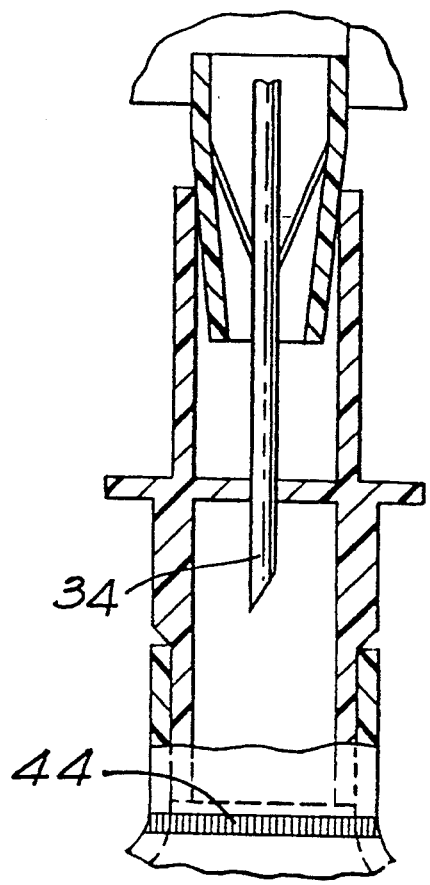
FIG. 6A is an enlarged view of the access passageway tube of FIG. 6.
Figure 7A:
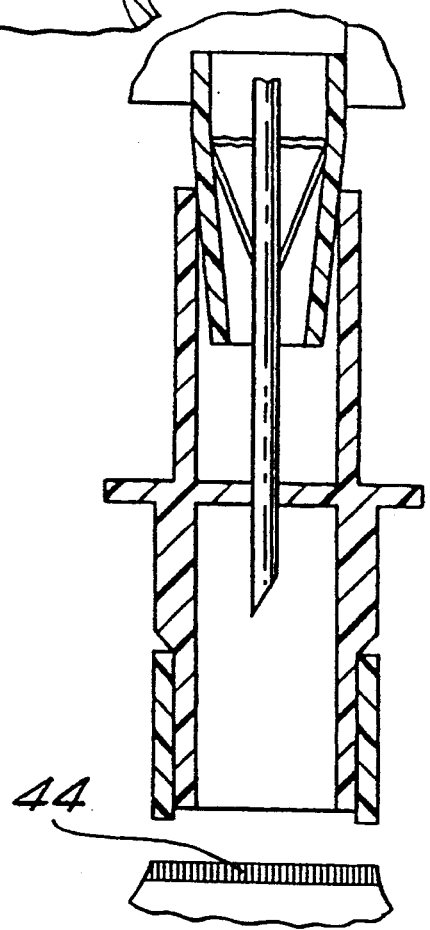
FIG. 7A is an enlarged view of the access passageway tube of FIG. 7.
Figure 7:
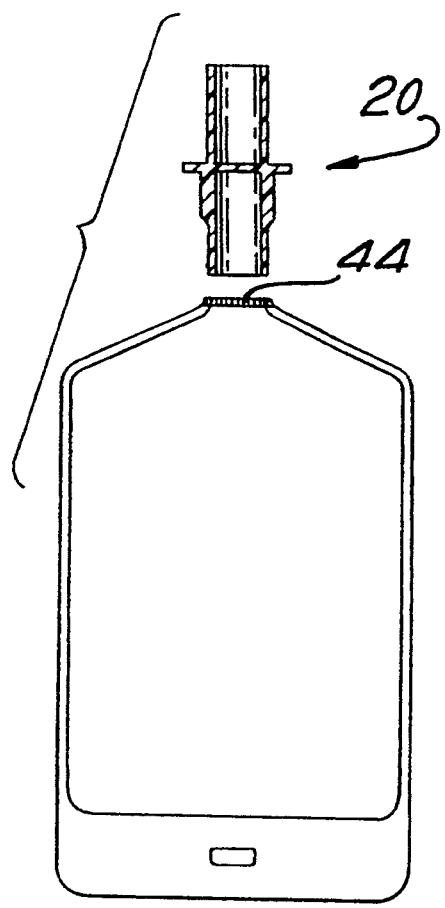
FIG. 7 is a schematic representation of the access passageway tube detached from the sealed neck portion of the filled flexible container.
Figure 8:
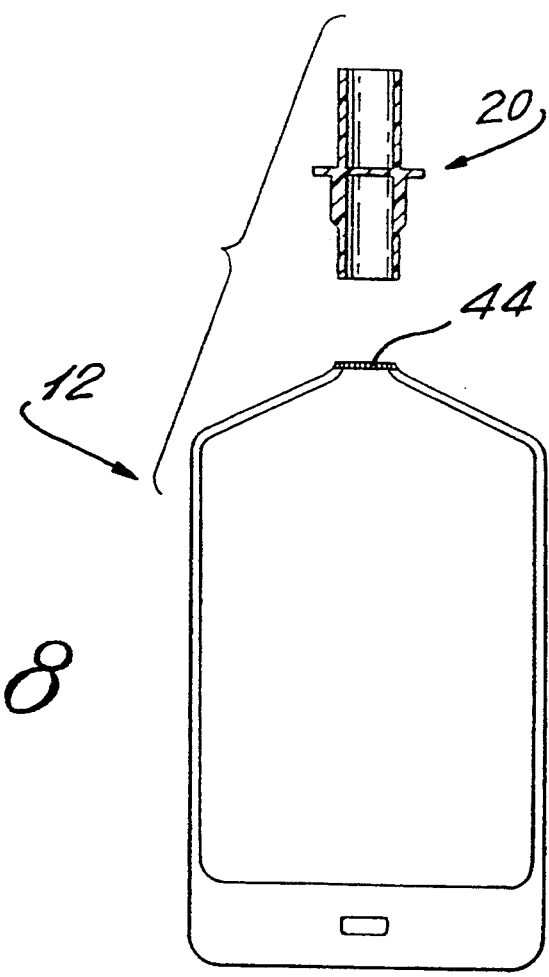
FIG. 8 is a schematic representation of the access passageway tube after the filling head has been completely withdrawn from one end of the tube and the filled and sealed flexible container is separated from the other end.

Thereafter, as can be seen in FIGS. 6 and 6A, the container is resealed at seal 44 to insure continued sterility of the container and its contents. After the container has been sealed, filling nozzle 34 and mandrel 38 and the unneeded portion of the access passageway 20 are separated from the container 12. Finally as seen in FIG. 8, the nozzle head is detached from the unneeded access passageway and positioned for a subsequent sterilization and filling procedure.

Sealing of container 12 at seal 44 can be affected in any convenient manner compatible with the container material and construction.

The present process is well suited for on-line filling operations of off-line sterilized empty containers. This process is useful for the sterilization of biological material which may degrade or loose potency if the material is sterilized in a traditional terminal sterilization manner after the container is filled.

The present process is also cost effective for the later on-line sterile filling of sterile empty containers previously sterilized by off-line batch sterilization of the empty containers.

The above discussion is intended by way of example only and is not intended to limit the invention in any way except in the spirit and scope of the appended claims.

We claim:

1. A method for the on-line sterile filling of a container with a sterile solution from a filling nozzle in a filling head, which comprises the steps of:
providing a container having an open end and a hollow body portion for receiving the sterile solution;
providing an access passageway tube, the access passageway tube having first and second open ends and a pierceable septum sealing the passageway at an intermediate position within the tube;
sealing the first open end of the access passageway tube in the open end of the container so as to close the hollow body portion of the container;
sterilizing the sealed hollow body portion of the container;
isolating an antechamber formed between the second open end of the access passageway tube and the septum from the surrounding environment by axially advancing and sealably seating the filling head within the second open end of the access passageway tube;
sterilizing the isolated antechamber for a time period sufficient to reduce the viable micro-organism population present to a predetermined level;
axially advancing a filling nozzle from the filling head through the isolated and sterilized antechamber and piercing the septum of the access passageway tube;
filling the sterilized hollow body portion of the container through the filling nozzle with the sterile solution; and
sealing the open end of the container between the hollow body portion and the filling nozzle before the filling nozzle is removed from the septum.

2. The method for on-line sterile filling in claim 1 wherein the antechamber is sterilized by a gas sterilization process.

3. A sterile fill method for filling a sterile container with a flowable material which comprises the steps of:
providing a closed sterile container that defines a hollow body portion for receiving the flowable material and is equipped with an access passageway that communicates with the hollow body portion the access passageway having first and second open ends and a pierceable septum sealing the passageway at an intermediate position within the passageway;
providing an axially moveable filling head having an advanceable filling nozzle;
isolating an antechamber formed between the second open end of the access passageway from the surrounding environment by sealably seating within the second opening of the access passageway the filling head;
sterilizing the isolated antechamber for a time period sufficient to reduce the viable micro-organism population present to a predetermined level;
advancing the filling nozzle so as to pierce the septum, and penetrate therethrough to provide communication with the hollow body portion;
dispensing the flowable material into the hollow body portion:
sealing the access passageway between the hollow body portion and the filling nozzle while the filling nozzle continues to penetrate the pierced septum; and
withdrawing the filling nozzle from the access passageway after sealing the access passageway.

4. The method for sterilizing in claim 3 wherein the antechamber is sterilized by a gas sterilization process.

* * * * *